US012672882B2

(12) United States Patent
　Lenzenhuber

(10) Patent No.:　US 12,672,882 B2
(45) Date of Patent:　Jul. 7, 2026

(54) MEDICAL TOOL HAVING CONNECTION RECOGNITION AND MEDICAL TOOL HAVING DECOUPLING RECOGNITION

(71) Applicant: Aesculap AG, Tuttlingen (DE)

(72) Inventor: Frederick Lenzenhuber, Tuttlingen (DE)

(73) Assignee: Aesculap AG (DE)

( * ) Notice: Subject to any disclaimer, the term of this patent is extended or adjusted under 35 U.S.C. 154(b) by 736 days.

(21) Appl. No.: 17/920,282

(22) PCT Filed: Apr. 20, 2021

(86) PCT No.: PCT/EP2021/060180
§ 371 (c)(1),
(2) Date: Oct. 20, 2022

(87) PCT Pub. No.: WO2021/214026
PCT Pub. Date: Oct. 28, 2021

(65) Prior Publication Data
US 2023/0172617 A1　　Jun. 8, 2023

(30) Foreign Application Priority Data
Apr. 22, 2020　　(DE) ..................... 10 2020 110 918.0

(51) Int. Cl.
*A61B 17/16*　　(2006.01)
*A61B 90/90*　　(2016.01)
*A61B 90/00*　　(2016.01)

(52) U.S. Cl.
CPC .............. *A61B 17/16* (2013.01); *A61B 90/90* (2016.02); *A61B 2090/031* (2016.02)

(58) Field of Classification Search
CPC ... A61B 17/16; A61B 90/90; A61B 2090/031; A61B 17/162; A61B 17/1626;
(Continued)

(56) References Cited

U.S. PATENT DOCUMENTS 3,124,017 A　*　3/1964　Brainard ............... B23B 39/165
　　　　　　　　　　　　　　　　　　　　　　408/46
4,319,577 A　　3/1982　Bofinger et al.
(Continued)

FOREIGN PATENT DOCUMENTS

CN　　101807243 A　　8/2010
CN　　105208962 A　　12/2015
(Continued)

OTHER PUBLICATIONS

Office Action (Notice of Reasons for Rejection) issued Dec. 10, 2024, by the Japanese Patent Office in corresponding Japanese Patent Application No. 2022-564034 and an English translation of the Office Action. (8 pages).
(Continued)

*Primary Examiner* — Tan-Uyen T Ho
*Assistant Examiner* — Bridget E. Rabaglia
(74) *Attorney, Agent, or Firm* — Buchanan Ingersoll & Rooney PC

(57) ABSTRACT

A medical tool, in the form of a rotatably drivable tool, in particular a cutting tool such as a trepanation tool, the tool having a drive portion which can be connected to a medical device for in particular interlockingly transmitting torque, and a cutting portion which can be coupled to the drive portion so as to transmit torque. The tool comprises an electronic assembly which is designed to be activated by the tool being connected to the medical device, preferably by an operation of plugging the tool into the medical device, and/or to be activated by the cutting portion being decoupled from the drive portion.

9 Claims, 8 Drawing Sheets

(58) Field of Classification Search
CPC ................ A61B 17/1695; A61B 90/98; A61B
2017/1602; A61B 17/1613; A61B
17/1615; A61B 17/1617; A61B 17/1622;
A61B 17/1624; A61B 17/1637; B25F
5/00; B25F 5/001; B25F 3/00; B25B
21/026; B25B 23/14; B25B 21/02; B25B
21/00
See application file for complete search history.

(56)                    References Cited

U.S. PATENT DOCUMENTS

| | | | |
|---|---|---|---|
| 4,456,010 | A | 6/1984 | Reimels et al. |
| 5,672,945 | A | 9/1997 | Krause |
| 2009/0065565 | A1 | 3/2009 | Cao |
| 2010/0034605 | A1 | 2/2010 | Huckins et al. |
| 2014/0224481 | A1* | 8/2014 | Scheibelmasser ...... E21B 47/12 166/250.01 |
| 2014/0276949 | A1 | 9/2014 | Staunton et al. |
| 2015/0022125 | A1* | 1/2015 | Takano ................... B25F 5/008 318/139 |
| 2018/0256287 | A1* | 9/2018 | Bosisio .................... A61C 5/42 |
| 2018/0353261 | A1 | 12/2018 | Mangelberger et al. |
| 2019/0000479 | A1* | 1/2019 | Harris ............... A61B 18/1442 |

FOREIGN PATENT DOCUMENTS

| | | |
|---|---|---|
| DE | 2916221 B1 | 3/1980 |
| DE | 69717800 T2 | 10/2003 |
| EP | 2581061 A1 | 4/2013 |
| JP | H09122145 A | 5/1997 |
| WO | 03013372 A2 | 2/2003 |
| WO | 2009138242 A2 | 11/2009 |

OTHER PUBLICATIONS

English Translation of the Written Opinion for International Application No. PCT/EP2021/060180, mailed Oct. 28, 2021, 9 pages.
German Search Report for German Application No. 10 2020 110 918.0, with partial translation, dated Nov. 27, 2020, 11 pages.
International Search Report and Written Opinion for International Application No. PCT/EP2021/060180, dated Oct. 28, 2021, 13 pages.
Office Action (The First Office Action) issued Jan. 20, 2026, by the State Intellectual Property Office of People's Republic of China in corresponding Chinese Patent Application No. 202180029862.5 and an English translation of the Office Action. (18 pages).

* cited by examiner

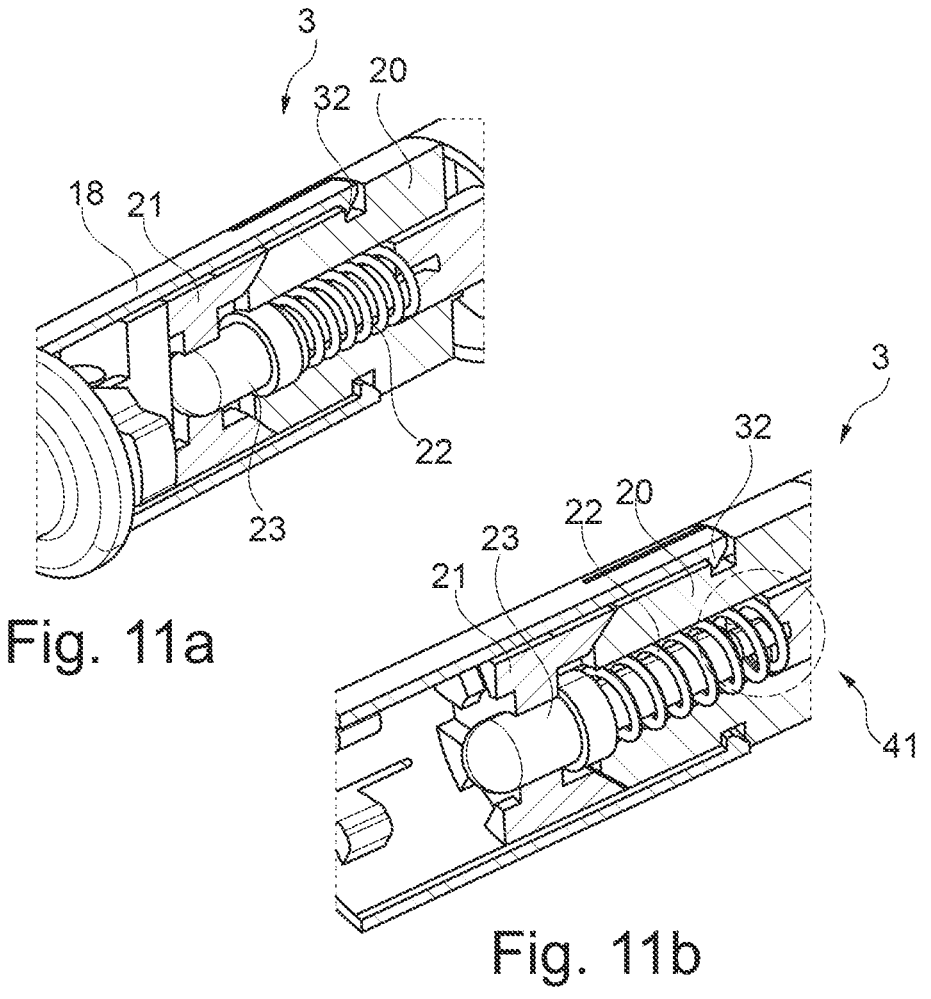
Fig. 11a
Fig. 11b
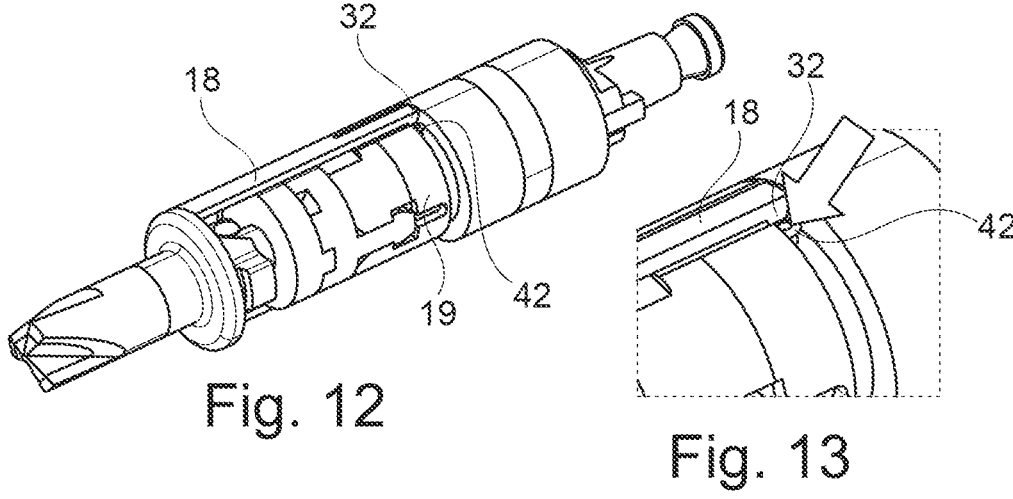
Fig. 12
Fig. 13

MEDICAL TOOL HAVING CONNECTION RECOGNITION AND MEDICAL TOOL HAVING DECOUPLING RECOGNITION

This application is a U.S. National Phase application of PCT International Application No. PCT/EP2021/060180, filed Apr. 20, 2021, which claims the benefit of DE102020110918.0, filed Apr. 22, 2020, both of which are incorporated by reference herein.

TECHNICAL FIELD

The present invention relates to a medical tool which is in the form of a rotatably drivable tool, in particular a cutting tool, preferably a trepanation tool, having a drive portion which can be connected to a medical device, preferably a surgical handpiece, for in particular interlockingly transmitting torque and a cutting portion which can be coupled to the drive portion so as to transmit torque.

Trepanation tools are used to introduce an operative opening in the cranial bone. In order to exclude damages to the dura positioned below the cranial bone, trepanation tools have a functional structure such that the cutting portion is decoupled from the actual drive, i.e., the drive portion, as soon as the cranial bone has been penetrated and before the dura positioned below the cranial bone can be damaged. This is usually achieved, as, for instance, in U.S. Pat. No. 4,456,010 A1 and in a generic tool, in that the cutting portion is displaceable relative to the drive portion in an axially confined manner between a first axial position in which the cutting portion and the drive portion are torque-coupled and a second axial position in which the cutting portion is torque-decoupled from the drive portion. In the cutting engagement, the cutting portion is kept in the first (torque-coupled) axial position by the cutting forces acting thereon, for instance, against the spring force of a spring, in particular against a spring-biased press button. If no cutting forces act on the cutting portion, the cutting portion is, for instance, by the spring force of the spring, in particular by the press button pressed (forward) by the spring bias, displaced to the second (torque-decoupled) axial position. Since no cutting forces counteract to the cutting portion as soon as the cranial bone has been penetrated, i.e., as soon as the trepanation operation has been performed, the pressure spring instantly releases the torque engagement between the drive portion and the cutting portion. Accordingly, the cutting portion is spring-biased in a torque-decoupled axial position.

The tool, in particular the trepanation tool, may be in the form of a reusable tool, i.e., a tool suited for multiple use with recycling. Alternatively, the (trepanation) tool may be in the form of a disposable tool (also known as a single use tool), i.e., as a tool suited for single use.

For the user it is often not possible to easily recognize which tool, for instance, which type of tools, which size of the tool, and/or which kind of use, i.e., reuse or single use tool, is concerned. Also, it has not been possible so far to automatically recognize medial tools, such as, for instance, hand tools or tools for insertion in surgical (hand) instruments. For identification of the tool, for instance, a label or an outer packaging must be inspected manually. Thus, it is not possible to exclude a wrong use of the tool used, for instance, the use of wrong tool parameters and/or the use of a tool not suited for the respective medical use. Also, due to the missing automatic documentation it is not possible to trace a combination of tools used or a wrong use, for instance, by overstrain of the tool, and product damage associated therewith. Furthermore, it is not possible to record the tool inventory without time-consuming inventory taking. Furthermore, the tools have to be examined for their functional capability and orderly condition prior to their use. For this purpose, the safe connection of all products to be used, in particular the safe fit of the tool in the handpiece, has to be examined in that the tool is pulled at manually for examining the coupling, which, however, entails latent danger of injury.

Therefore, it is an object of the invention to avoid or to reduce the disadvantages of the state of the art and to provide a medical tool, in particular a trepanation tool, enabling an automatic tool recognition and/or an automatic tool documentation and thus reducing the risk of a possible wrong use of the tool.

Overview of the Invention

The object of the invention is solved by the subject matters of the independent claims. Advantageous further developments are the subject matter of the subclaims.

More precisely, the object of the invention is solved by a medical tool which is in the form of a rotatably drivable tool, in particular a cutting tool, preferably a trepanation tool, having a drive portion (torque introducing unit) which can be connected to a medical device for in particular interlockingly transmitting torque and a cutting portion which can be coupled to the drive portion so as to transmit torque. The tool comprises a (first) electronic assembly which is designed to be activated by the tool being connected to the medical device, preferably by an operation of plugging the tool into the medical device. The tool as such is accordingly equipped with an electronic assembly for acquiring information. The electronic assembly can be activated automatically in that the tool is plugged into the medical device.

In other words, the tool (trepanation tool) comprises an integrated electronic assembly which is activated when the tool is connected/coupled to the device (surgical handpiece), in particular plugged into the device, and which is deactivated when the tool and the device are unconnected/decoupled from each other, in particular the tool is not plugged into the device. This means that an activation of the electronic assembly is dependent on a coupling of the tool and the device, whereby advantageously a tool coupling can be recognized automatically. This has also the advantage that the safe fit between the tool and the device need no longer be examined manually, for instance, by pulling at the tool, since a feedback about the successful coupling can take place by the activation of the electronic assembly.

In accordance with an advantageous further development the electronic assembly may have a storage device in which tool-specific data, such as, for instance, tool operating parameters, tool state data, application parameters, serial number, article number, minimum durability date (MDD), lot number (LOT), and/or further information are stored which are, during activation of the electronic assembly, preferably transmitted and/or output to an external processing unit and/or to a user of the tool. This means that the tool-specific data, in particular for recognizing the tool, are provided to be externally acquirable during activation of the electronic assembly. In other words, by the activation of the electronic assembly it is possible to transmit and further process the data stored, so that an automatic tool recognition may be provided The processing unit may, for instance, be a terminal, such as a tablet or a smartphone, or a control device or an internet-based platform, such as a cloud. Due to the automatic tool recognition it is possible to simultaneously accomplish an automatic documentation. Moreover, it is possible to automatically set individual tool parameters, such as the number of revolutions or the energization, based on the tool-specific data transmitted, which prevents wrong use. Furthermore, it is, for instance, possible to detect multiple use of the tool. Thus, the user may, for instance, be informed if the tool is only suited for single use but has already been inserted. This information is stored. The user may possibly also be informed intraoperatively.

In accordance with a preferred embodiment the first electronic assembly may be arranged in a stationary component of the tool. This has the advantage that the electronic assembly need not be co-rotated during the cutting operation.

In accordance with a preferred embodiment the electronic assembly may have a switch which can be activated mechanically by the connecting of the tool. In other words, the switch is designed such at the drive portion of the tool which is to be connected to the device that the switch, in a non-activated state, projects (axially or radially) from the drive portion and is, by the connecting of the drive portion with the medical device, displaced relative to the drive portion, in particular pressed into the drive portion for activating the switch. Preferably, the drive portion comprises a standardised interface, such as a Hudson connection. Due to the arrangement of the mechanically activated switches at the drive portion the switch is activated automatically when the tool is inserted into the medical device since the tool has to be received snugly by the device for guaranteeing a safe fit. Therefore, the switch is activated mechanically when used with any (conventional) device if the drive portion rests on the device in the region of the switch. Since the interface between the tool and the device is usually standardised, the activation of the electronic assembly takes place independently of the rest of the construction of the device.

In accordance with an advantageous further development of the preferred embodiment the switch can, by the connecting of the tool, be activatable mechanically such that the switch closes an electric circuit of the electronic assembly in an activated switching position and opens it in a non-activated switching position. Preferably, the electronic assembly comprises a communication device for generating a radio connection which transmits a radio signal with the tool-specific data during activation of the electronic assembly, i.e., during closing of the electric circuit. For instance, the communication device can transmit the radio signal actively, i.e., by WLAN or Bluetooth Low Energy (BLE), or by a Low-Power Wireless Network Protocol, such as LoRaWAN (Long Range Wide Area Network), or passively, for instance, by RFID or NFC. The radio signal can also be transmitted by another radio standard which is suited for (contact-free) data transfer and is not restricted to any of the radio standards mentioned nor to a particular frequency range. When the electric circuit is interrupted when the tool is decoupled from the device, the communication device does no longer transmit a radio signal or is no longer reachable in the case of passive technologies. In other words, the electronic assembly may, for instance, comprise an RFID chip, an NFC chip, a WLAN module and/or a Bluetooth Low Energy chip, which are all designed to transmit the radio signal to an associated receiver being in a vicinity of the tool when the electronic assembly is activated. The receiver can forward the data transmitted by the radio signal to further terminals. In accordance with a further preferred further development of the preferred embodiment the communication device may be arranged in a plastic housing of the tool, whereby radio permeability exists in an advantageous manner.

In accordance with a preferred embodiment the switch can, by the connecting of the tool, be displaceable in the axial direction between the activated switching position and the non-activated switching position. The insertion direction of the tool usually corresponds to the axial direction, so that an axial activation of the switch can be accomplished easily. The switch may preferably project from an axial abutment face of the tool on which the device rests in the coupled state. It can thus be ensured that the switch is only activated in an end position of the tool in the device in which the tool and the device are connected in an axially secured manner so as to avoid that the electronic assembly is activated when the plugging operation has not yet been concluded and the tool has no safe fit.

In accordance with an alternative preferred embodiment the switch can, by the connecting of the tool, be displaceable in the radial direction between the activated switching position and the non-activated switching position. The switch may preferably project from a radial outer circumference of the drive portion on which the device rests in the coupled state. Since the drive portion is often plugged into the device such that it rests radially outward at the radial inner diameter of the device, an automatic activation can be ensured with the switch which is to be activated radially by means of the connecting of the tool to the device.

In accordance with a preferred embodiment the electronic assembly may comprise a feedback device and/or be connectable to an external feedback means. The feedback device and/or the feedback means may in particular be designed such that an acoustic and/or visual feedback is output when the electronic assembly is activated or is being activated. Thus, the user obtains an automatic confirmation about the successful connection, so that the safe fit need no longer be examined by touching. The feedback device may, for instance, be designed as a lamp, such as an LED preferably visible from outside in the drive portion, and/or as an acoustic signaller whose shining and/or sound render feedback about whether the tool is or is not (correctly) connected to the device, i.e., confirms successful connecting. The external feedback means may, for instance, be designed as a control device or terminal coupled in particular via the radio connection, such as a smartphone or a tablet which informs about whether the tool is or is not (correctly) connected to the device.

In accordance with a further aspect of the invention which may be provided in combination with the above-described aspect or independently thereof, the object of the invention is solved by a medical tool which is designed as a rotatably drivable tool, in particular as a cutting tool, preferably a trepanation tool, having a drive portion (torque introducing unit) which can be connected to a medical device for in particular interlockingly transmitting torque and a cutting portion which can be coupled to the drive portion so as to transmit torque. The tool comprises a (second) electronic assembly which is designed to be activated by the cutting portion being decoupled from the drive portion. In particular, the cutting portion is displaceable relative to the drive portion, for instance, against a spring-biased pressure button, in an axially confined manner between a first axial position in which the cutting portion and the drive portion are torque-coupled and a second axial position in which the cutting portion is torque-decoupled from the drive portion. The second electronic assembly is designed and arranged such that it is deactivated in the first axial position and activated in the second axial position. In other words, a switch path defined by the confined axial relative displacement between the drive portion and the cutting portion is used to activate the electronic assembly.

This has the advantage that the coupling and/or decoupling operations of the (trepanation) tool can be acquired and/or documented (automatically). Advantageously, the number of decouplings per operation can thus be recorded. This has also the advantage that, even in tools with are not energized and in which the attachments are decoupled from the actual drive, the decoupling may be used for closing or interrupting an electric circuit and hence for identification, which can advantageously be used for the digitalisation of (medical) tools and devices.

The second electronic assembly can, for instance, be mechanically switchable by the decoupling of the cutting portion from the (drive portion) such that an electric circuit of the electronic assembly is closed (or opened) in an activated switching position and opened (or closed) in a non-activated switching position.

In accordance with a preferred embodiment the second electronic assembly may have a second switch which is preferably in the form of a push button, and which can, by an activating portion which can be rotatably coupled to the cutting portion, be mechanically activated such that it acquires the number of revolutions of the cutting portion, in particular after the decoupling of the cutting portion from the drive portion. For instance, the push button arranged preferably at a non-rotating component of the tool, for example in the form of a dome or a ramp, may be designed such that it is mechanically activated by an activating portion which can be rotatably coupled to the cutting portion, for instance, in the form of an outer sleeve, of the tool in correspondence with the number of revolutions, e.g. with every revolution, of the cutting portion. In accordance with an advantageous further development of the preferred embodiment the activating portion may be designed such that it is rotatably decoupled from the cutting portion in the first axial position and rotatably coupled to the cutting portion in the second axial position. This ensures that the activating portion only co-rotates (with the cutting portion) when the cutting portion is decoupled from the drive portion. Thus, only the revolutions after the decoupling are acquired. According to experience the number of (rest) revolutions after the decoupling has turned out to be particularly meaningful with respect to wear and lifetime of the tool. Preferably the number of decouplings and/or the number of rest revolutions is stored in a storage device of the electronic assembly and/or preferably in combination with tool-specific data, such as the serial number or the article number, transmitted to the external processing unit. The transfer of information can, for instance, take place in real time or in line with demand (just in time). In other words, the activating portion is arranged and designed such that the second switch/push button is activated in correspondence with the number of revolutions of the cutting portion. For instance, the activating portion may be formed by a plurality of catch elements, particularly catch elements distributed in the circumferential direction, so that the switch/push button activates several times per revolution. Thus, incomplete revolutions of the cutting portion can also be acquired. Due to a plurality of catch elements a mechanical catch mechanism is ensured at the same time. In other words, the number of revolutions corresponds, for instance, to a quotient from the number of activations of the second switch and the number of catch elements.

Preferably, the second electronic assembly may comprise, for generating a radio connection, a (second) communication device arranged in a plastic component of the tool or be connected with the communication device of the first electronic assembly, which is further preferably designed such that it transmits a radio signal with data about the decoupling operation during activation of the second electronic assembly. Preferably, the second electronic assembly comprises a (second) storage device or is connected to the storage device of the first electronic assembly so as to acquire the number of activations of the second electronic assembly (and thus the number of decouplings of the cutting portion) and/or the number of (rest) revolutions.

In accordance with a preferred embodiment the second electronic assembly may be arranged in a stationary component of the tool. This has the advantage that the electronic assembly need not be co-rotated during the cutting operation.

In accordance with a further aspect of the invention the drive portion may have a socket preferably formed of plastics which is in particular connectable directly to the medical device and may have a follower preferably formed of metal which is connected to the socket in an axially secured and interlockingly non-rotatable manner. Specifically, the (first) electronic assembly may be arranged in the socket. Alternatively, the socket and the follower may be formed of plastics. Further alternatively, the socket may be formed of metal and the follower of plastics.

In accordance with a preferred embodiment the socket may comprise an axial securing portion, for instance, in the form of latching indentations in which a counter securing portion formed at the follower, for instance, in the form of latching hooks engages for axial securing. In accordance with a preferred embodiment the socket may comprise a torque transfer section, for instance, in the form of power transmission indentations in which a counter portion formed at the follower, for instance, in the form of webs, engages for interlocking torque transmission. In other words, the functions of axial securing and of torque transmission are designed at separate portions of the follower. Preferably, the latching indentations and/or the power transmission indentations are of symmetric arrangement. In accordance with a particularly preferred embodiment the axial securing portion may be arranged distally to the torque transmission portion so as to enable a suitable power flow. The torque transmission portion is thus arranged closer to the cutting portion than the axial securing portion.

In accordance with a further aspect of the invention the cutting portion may comprise a basic portion which is preferably coupled directly to the drive portion, and an engagement portion which is formed separately thereof and preferably carries the blades and which is connected to the basic portion in an axially secured and/or non-rotatable manner at a (first) interface, for instance, in the form of a thread. Preferably, the interface is designed such that the engagement portion is applied by rotating contrary to its direction of rotation in cutting engagement with the basic portion so as to avoid unintended loosening by the cutting forces. It is particularly preferred if the interface is designed such that it is connectable to engagement portions of different structure and/or size. It is further preferred that the cutting portion comprises a sleeve portion formed separately of the engagement portion and mounted at a (second) interface at an outer diameter of the engagement portion. Specifically, the engagement portions of different structure and/or size may have the same outer diameter. Due to the modular structure and the use of the same parts with different types of tools and/or sizes of tools it is possible to reduce the manufacturing costs of the tool.

In accordance with a further aspect of the invention the cutting portion may comprise a plastic dome at which insertion parts forming the blades, in particular of metal, are firmly mounted, for instance, by thermal punching. Thus, apart from the blades formed by metal sheets, the entire (trepanation) tool can be manufactured cost-efficiently from plastics.

BRIEF DESCRIPTION OF THE FIGURES

FIGS. 11 to 13 are different perspective, partially sectional illustrations of the tool in a second embodiment.

In the following, embodiments of the present disclosure will be described on the basis of the associated Figures. The Figures are merely of schematic nature and serve the understanding of the invention. Same elements are marked with the same reference numbers.

FIG. 1 shows a medical tool 1 connectable to a medical device 2, such as a surgical handpiece. In FIG. 1a the tool 1 is not connected to the medical device 2, i.e., is decoupled from the device 2. In FIG. 1b the tool 1 is connected to the medical device 2, i.e., coupled to the device 2. In the illustrated embodiments the tool 1 is in the form of a rotatably drivable tool. For this purpose, the tool 1 is connected to the device 2 for transmission of a torque for driving the tool 1. The tool 1 may in particular be designed as a cutting tool.

Figure 1A:
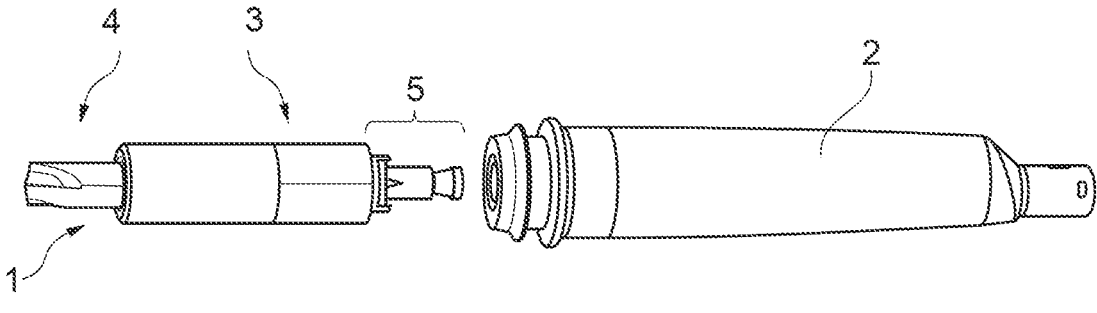
FIGS. 1a and 1b are perspective illustrations of the connecting of a tool in accordance with the invention to a medical device according to a first embodiment of the invention for activating an electronic assembly.
Figure 1B:
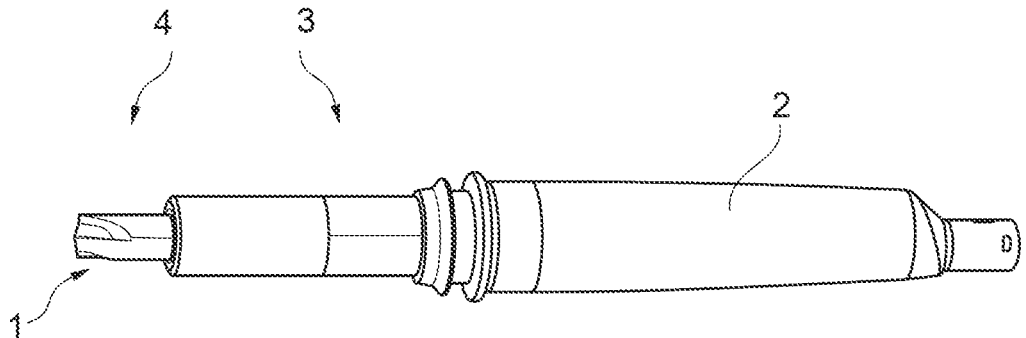

The tool 1 comprises a drive portion 3 which is partially plugged into the device 2 and engages the device 2 in an interlockingly non-rotatable manner. Furthermore, the tool 1 comprises a cutting portion 4 enlarging the drive portion 3 in the axial direction. Blades for the cutting operation are arranged at the cutting portion 4. The drive portion 3 comprises a coupling portion 5 which forms that part of the drive portion 3 which is plugged completely into the device 2 in the connected state. The coupling portion 5 is, in the illustrated embodiments, formed as a Hudson connection 6 which is used universally as an interface for handpieces.

Figure 3:
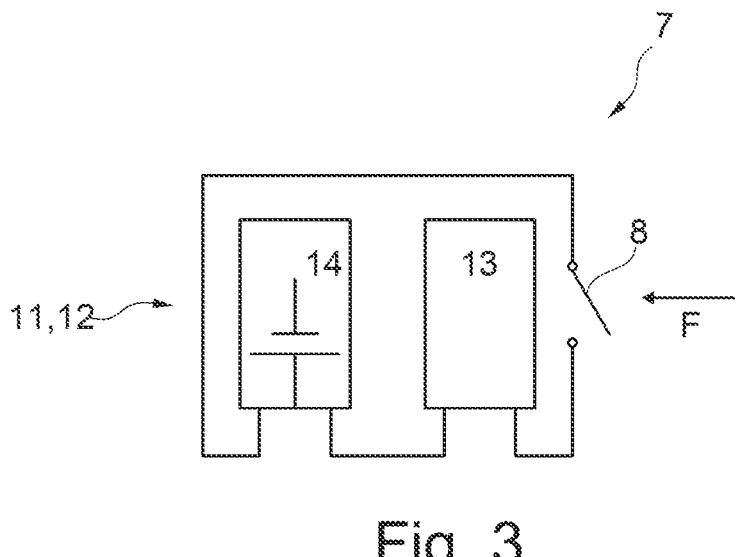
FIGS. 3 and 4 show schematic illustrations of a communication device of the electronic assembly of the tool.
Figure 4:
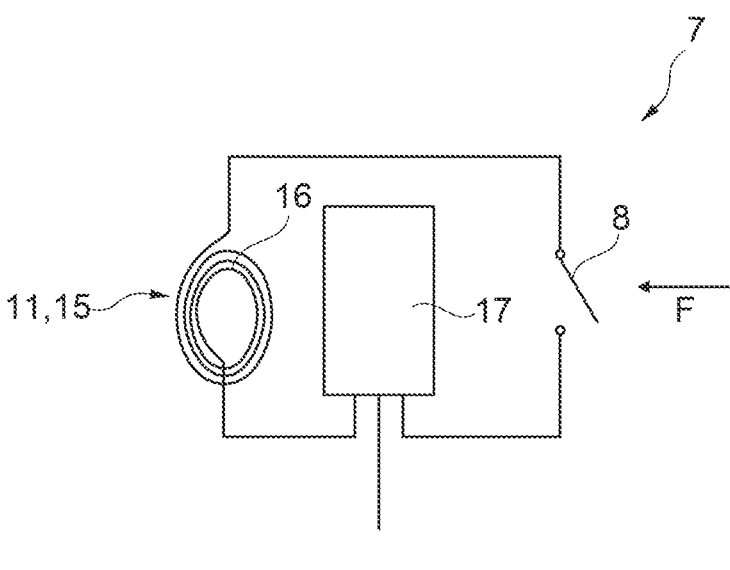

The tool 1 comprises an electronic assembly 7 (cf. FIGS. 3 and 4). The electronic assembly 7 is designed to be activated by the tool 1 being connected to the medical device 2, preferably by an operation of plugging the tool 1 into the medical device 2. Preferably, the electronic assembly 7 has a switch 8 which is, by the connecting of the tool 1, mechanically activatable such that the switch 8 closes an electric circuit of the electronic assembly 7 in a first switching position and opens it in a second switching position.

Figure 2A:
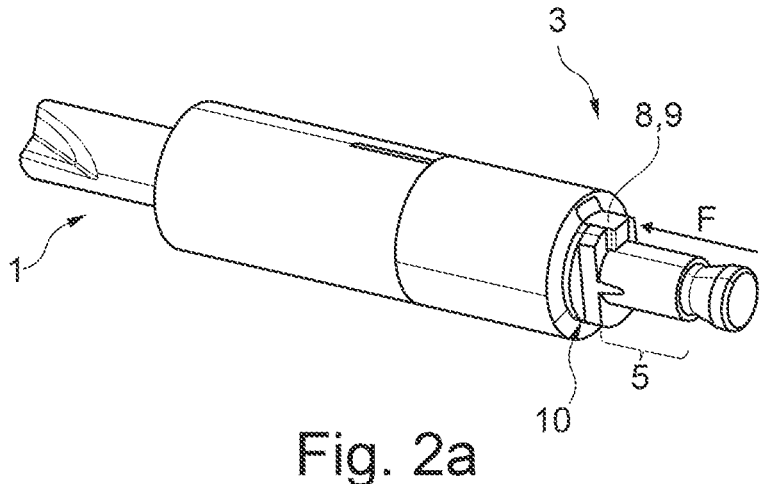
FIGS. 2a and 2b show perspective illustrations of the tool with a switch of the electronic assembly in two different embodiments.
Figure 2B:
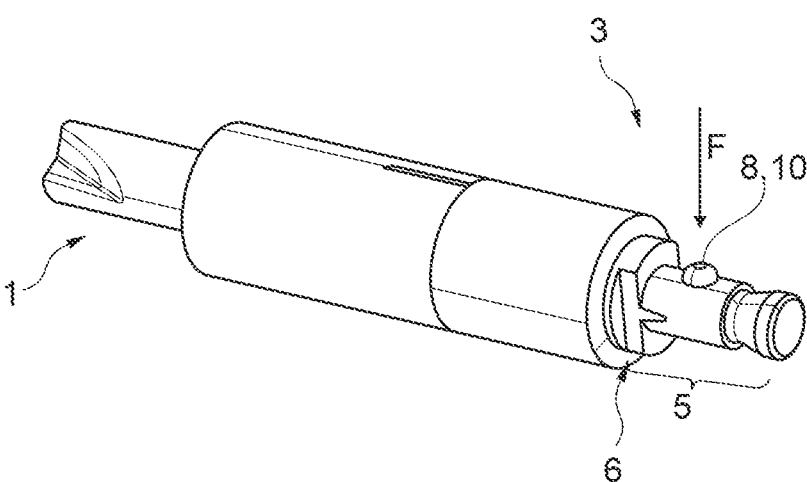

In FIG. 2a the switch 8 is formed as an axial switch 9 which is displaceable in the axial direction for activation. The axial switch 9 is arranged at an axial abutment face of the coupling portion 5 and projects axially in the direction to the device 2. At the abutment face the device 2 rests in the state connected to the tool 1 and thus activates the axial switch 9. When the tool 1 is connected to the device 2, the axial switch 9 is activated. When the tool 1 is not connected to the device 2, the axial switch 9 is not activated. In FIG. 2b the switch 8 is formed as a radial switch 10 which is displaceable in the radial direction for activation. The radial switch 10 comprises a hemispherical dome shape. The radial switch 10 is arranged at a radial outer circumference of the coupling portion 5 and projects radially outwardly. In the state connected to the tool 1 the device 2 is pushed onto the radial outer circumference and thus activates the radial switch 10. When the tool 1 is connected to the device 2, the radial switch 10 is activated. When the tool 1 is not connected to the device 2, the radial switch 10 is not activated. The switch 8 is thus arranged at the coupling portion 5 such that it is mechanically automatically activated in the connected state by the device 2 and is automatically non-activated in the unconnected state.

The electronic assembly 7 may have a storage device in which tool-specific data, such as tool operating parameters, tool state data, application parameters, serial number, article number, minimum durability date (MDD), lot number (LOT), and/or further information are stored. The electronic assembly 7 may have a communication device 11 for generating a radio connection. The communication device 11 is arranged such that, during activation of the electronic assembly 7, i.e., during closing of the electric circuit, it transmits a radio signal with the tool-specific data stored in the storage device.

FIG. 3 shows a possible structure of the communication device 11 which is designed as a Bluetooth Low-Energy unit 12. Alternatively, the communication device 11 may also be designed as another radio module, for instance, as a W-LAN module or a Lo-RA-WAN module (Long Range Wide Area Network module). In the communication device 11 the electric circuit is closed when the switch 8 is activated, and a Bluetooth Low-Energy chip 13 is connected to a battery 14. The Bluetooth Low-Energy unit 12 can transmit a radio signal actively to an associated receiver being in the vicinity of the tool 1 when the electric circuit is closed. When the electric circuit is interrupted by the decoupling of the tool 1 from the device 2, the communication device 11 does no longer send a radio signal. FIG. 4 shows an alternative possible structure of the communication device 11 which is designed as an RFID or NFC unit 15. When the switch 8 is activated, the electric circuit is closed in the communication device 11 and a coil 16 is connected to a storage 17, for instance, an EEPROM (electrically erasable programmable read-only memory). In contrast to the structure shown in FIG. 3, no battery is necessary, so that the lifetime of the electronic assembly 7 is not dependent on the battery lifetime. The RFID or NFC unit 15 can transmit a radio signal passively. The storage 17 can be read out via the coil 16. The radio signal can be transmitted by the NFC unit 15, for instance, to a receiver arranged in the device 2 and be forwarded from there. By the connecting of the tool 1 to the device it is, as schematically shown in FIGS. 3 and 4, possible to forward tool-specific data stored in the storage device to peripheral devices. There in turn the data are further processed and output to the user, stored in the cloud, and/or put online.

Figure 5:
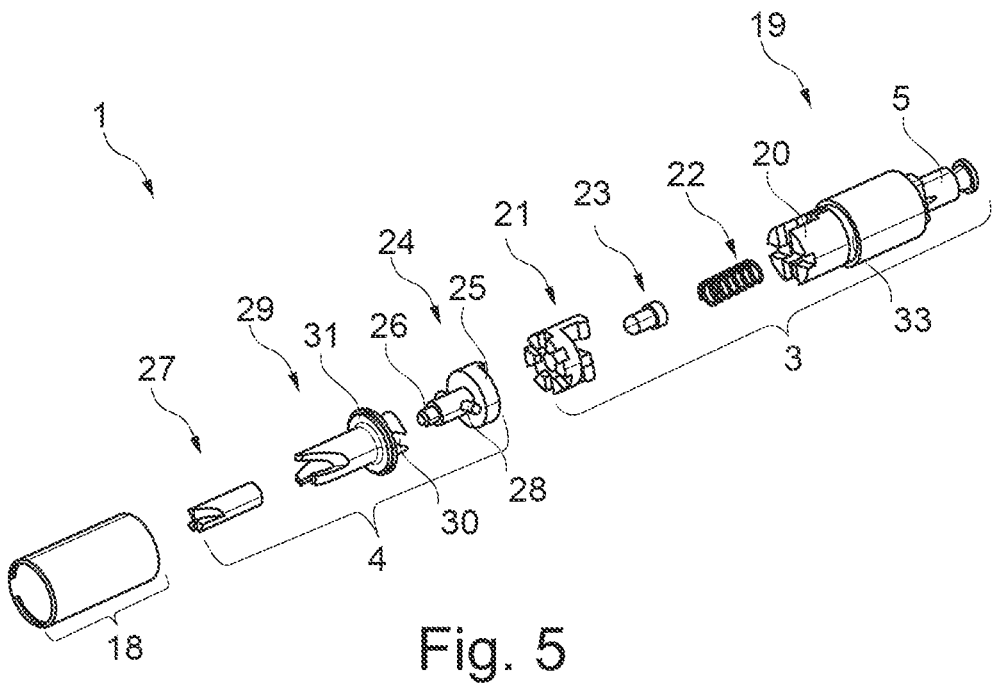
FIGS. 5 and 6 show perspective illustrations of the tool in the first embodiment.

A structure of the tool 1 is explained with reference to FIGS. 5 and 6. The tool 1 may be divided functionally into the drive portion 3, the cutting portion 4, and a sleeve portion 18.

The drive portion 3 (cf. also FIGS. 7 to 10) comprises a socket 19 at which the coupling portion 5 is formed. The socket 19 is formed as a plastic component. The electronic assembly 7 is accommodated in the socket 19. A connecting portion 20 is formed at a proximal end of the socket 19. The drive portion 3 comprises a follower 21 which is connected in an axially secured and non-rotatable manner to the connecting portion 20. In the connecting portion 20 a spring 22 is accommodated, against the spring force of which the cutting portion 4 is displaceable axially between the first axial position and the second axial position. A pressure button 23 is arranged axially between the follower 21 and the connecting portion 20. The pressure button 23 reaches axially through a central recess in the follower 21.

The cutting portion 4 comprises a basic portion 24. The basic portion 24 serves for power transmission/torque transmission and comprises a follower 25. The follower 25 of the cutting portion 4 can interlockingly engage the follower 21 of the drive portion 3 in a non-rotatable manner, so that a torque can be transferred from the drive portion 3 to the cutting portion 4. In the first axial position the follower 25 engages in the follower 21. The basic portion 24 comprises a first interface 26. Via the first interface 26 a first engagement portion 27 of the cutting portion 4, here in the form of an internal cutter, can be connected to the basic portion 24 so as to transmit torque. The first interface 26 is formed as a thread on which the first engagement portion 27 can be screwed preferably against the cutting direction/drive direction of the tool 1.

The first engagement portion 27 is in particular secured by a tightening torque. The basic portion 24 comprises a second interface 28. Via the second interface 28 a second engagement portion 29 of the cutting portion 4, here in the form of an external cutter, can be connected to the basic portion 24 so as to transmit torque. The second interface 28 is formed as a transverse pin onto which the second engagement portion 29 can be pushed. In the second engagement portion 29 a groove 30 is formed which connects the second engagement portion 29 interlockingly with the transverse pin in a non-rotatable manner. The second engagement portion 29 comprises a flange 31 projecting radially outwardly. The flange 31 is formed to be radially circumferential.

The sleeve portion 18 is preferably formed of plastics. The sleeve portion 18 forms an outer diameter of the tool 1. The sleeve portion 18 rests with its proximal end on the flange 31 of the cutting portion 4. The sleeve portion 18 rests with its distal end at an axial abutment face provided by the socket 19. The sleeve portion 18 comprises a journal 32 projecting radially inwardly and engaging in a circumferential groove 33 in the connecting portion 20 and thus securing the sleeve portion 18 axially.

Figure 6:
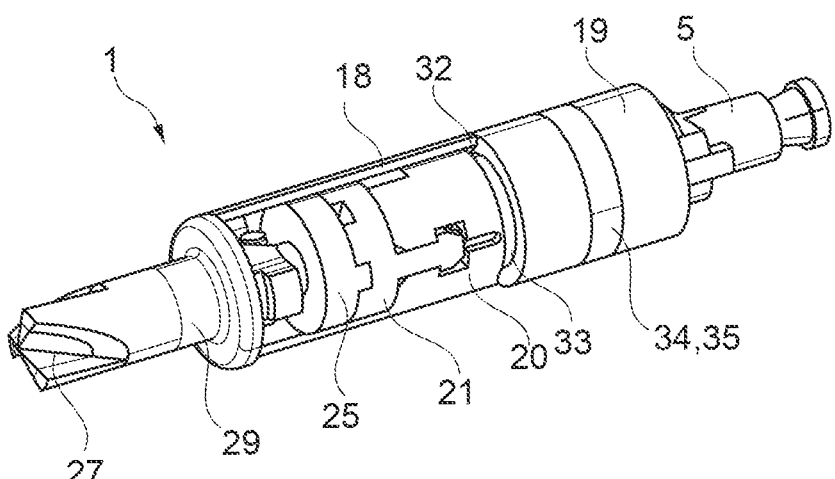
Figure 7:
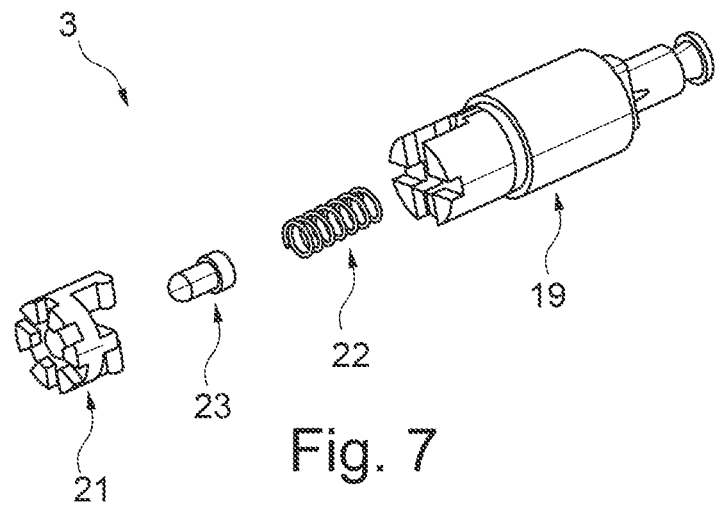
FIGS. 7 to 10 show perspective illustrations of a drive portion of the tool and its individual parts.
Figure 8:
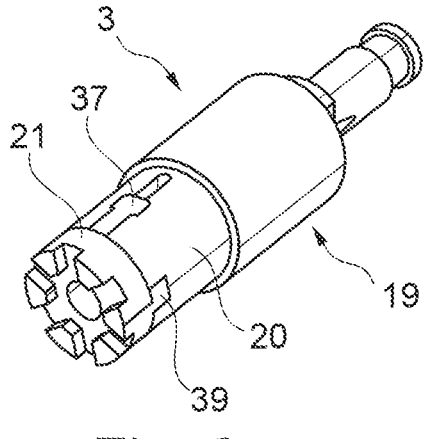
Figure 9:
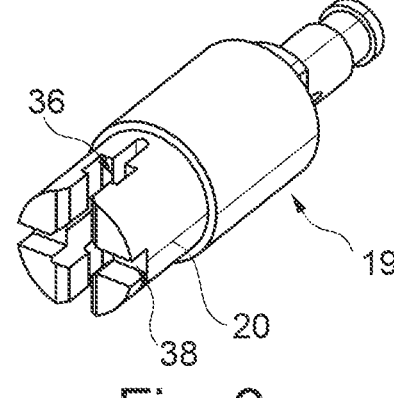
Figure 10A:
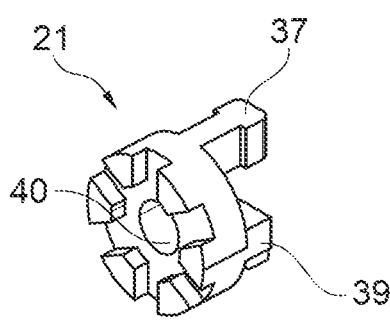
Figure 10B:
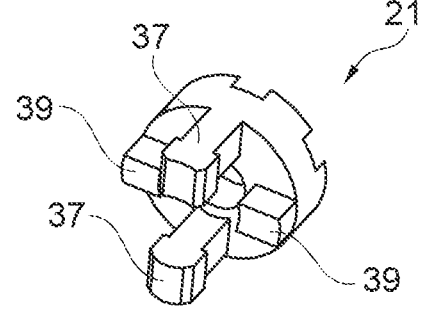

In the embodiment illustrated in FIG. 6 the electronic assembly 7 comprises a feedback device 34. The feedback device 34, here in the form of an LED 35, is arranged in the socket 19 and shines when the electronic assembly 7 is activated. The LED 35 can, for instance, emit green light when it is correctly coupled, and red light, when it is incompletely coupled. The LED 35 can also emit a flashing light or a permanently shining light. The LED 35 can also shine in other colours. The feedback device 34 may, for instance, also comprise a plurality of LEDs, one of which renders feedback about the successful coupling and another of which renders feedback about faulty coupling. Alternatively or additionally the feedback device 34 can output an acoustic feedback when the electronic assembly 7 is activated or is being activated. For instance, the frequency/pitch of the acoustic feedback or the interval between several acoustic signals/feedbacks may differ with successful coupling and unsuccessful coupling.

A structure of the drive portion 3 will be described with reference to FIGS. 7 to 10. The drive portion 3 is formed in particular by the follower 21 designed as a metal component and by the socket 19 designed as a plastic component. Alternatively, the socket 19 and the follower 21 may be designed as metal components. Further alternatively, the socket 19 and the follower 21 might be designed as plastic components. Further alternatively, the socket might be designed as a metal component and the follower 21 as a plastic component. The spring 22 and the press button 23 are irrelevant for the transmission of the forces and the torques.

The socket 19 and the follower 21 are connected with each other in an axially secured manner. For this purpose, the socket 19 comprises one and/or a plurality of latching indentations 36 into which one and/or a plurality of latching hooks 37 of the follower 21 engage. The follower 21 accordingly engages behind the socket 19 in the axial direction. The latching indentations 36 are arranged symmetrically, i.e., opposing each other in the circumferential direction. The latching hooks 37 are arranged symmetrically, i.e., opposing each other in the circumferential direction. The socket 19 and the follower 21 are connected to each other so as to transmit torque. For this purpose, the socket 19 comprises one and/or a plurality of power transmission indentations 38 in which one and/or a plurality of webs 39 of the follower 21 engage. The power transmission indentations 38 are arranged symmetrically, i.e., opposing each other in the circumferential direction. The webs 39 are arranged symmetrically, i.e., opposing each other in the circumferential direction. The webs 39 are positioned in the circumferential direction between the latching hooks 38. The follower 21 comprises a central recess 40 through which the press button 23 can reach for decoupling, i.e., for disengaging the cutting portion 4.

In the illustrated embodiments the tool 1 is designed as a trepanation tool. The functioning of a trepanation tool will be explained with reference to FIGS. 11a and 11b. In the tool 1 the cutting portion 4 is displaceable relative to the drive portion 3 in an axially confined manner between a first axial position (cf. FIG. 11a) in which the cutting portion 4 and the drive portion 3 are torque-coupled, and a second axial position (cf. FIG. 11b) in which the cutting portion 4 is torque-decoupled from the drive portion 3. Thus, the cutting portion 4 can be decoupled from the actual drive. In the cutting engagement the cutting portion 4 is pressed by the cutting forces acting thereon to the first axial position against the spring force of the spring 22. The pressure knob 23 mounted in the drive portion 3 is displaced axially and the spring 22 is biased. If no cutting forces act on the cutting portion 4, the cutting portion 4 is pressed to the second axial position by the spring force of the spring 22. By the spring bias the pressure button 23 is displaced in the direction toward the cutting portion 4, so that it pushes the (output-side/torque-receiving) follower 25 of the cutting portion 4 out of engagement with the (input-side/torque-transmitting) follower 21 of the drive portion 3.

In FIG. 11b the axial relative movement of a switching path between the first axial position and the second axial position is marked by a dashed circle. This axial relative movement can be used to activate a second electronic assembly 41. In accordance with a further aspect of the invention the tool 1 comprises the second electronic assembly 41 which is designed to be activated by the decoupling of the cutting portion 4 from the drive portion 3. This means that the second electronic assembly 41 is designed such that it is deactivated when the cutting portion 4 is in the (coupled) axial position relative to the drive portion 3, and is activated when the cutting portion 4 is in the second (decoupled) axial position relative to the drive portion 3. The second electronic assembly 4 in particular comprises a non-illustrated switch which is activated mechanically by the axial displacement of the cutting portion 4, in particular the pressure button 23.

In FIGS. 12 and 13 a further embodiment of the tool 1 is illustrated. The second electronic assembly 41 has a second switch 42. The second switch 42 is designed as a push button. The second switch 42 can be activated mechanically by the cutting portion 4 such that it acquires the number of revolutions of the cutting portion 4, in particular after the decoupling of the cutting portion 4 from the drive portion 3. The second switch 42 comprises a hemispherical dome shape. The second switch 42 may also be designed in the form of a ramp. The second switch 42 is arranged on a radial outer circumference of the drive portion 3, here in a region of the connecting portion 20, and projects radially outwardly. The second switch 42 is arranged in the groove 33. The journal 32 at the sleeve portion 18 serves as an activating portion, so that the second switch 42 is actuated by the journal 32 in correspondence with the number of revolutions of the sleeve portion 18. In other words, the number of revolutions corresponds, for instance, to a quotient from the number of activations of the second switch 42 and the number of journals 32 (latching elements). The sleeve portion 18 may, for instance, be of symmetric design, i.e., comprise two journals 32 opposing each other in the circumferential direction. Then, the second switch 42 is activated twice per revolution of the sleeve portion 18. It is thus possible to also acquire half revolutions of the sleeve portion 18. Due to a plurality of journals 32 a mechanical catch mechanism is ensured at the same time. Thus it is possible to acquire a number of revolutions of the sleeve portion 18. The sleeve portion 18 is in particular designed such that it is rotatably decoupled from the cutting portion 4 in the first axial position and rotatably coupled to the cutting portion 4 in the second axial position.

Figure 14:
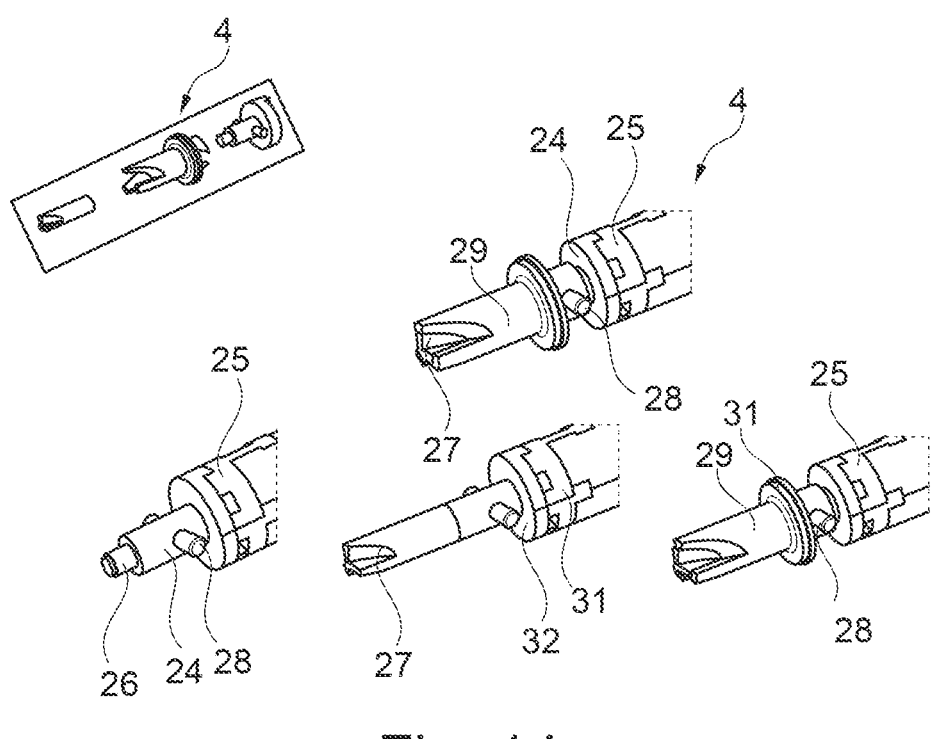
FIGS. 14 to 16 are perspective illustrations of a cutting portion of the tool in different sizes.
Figure 15A:
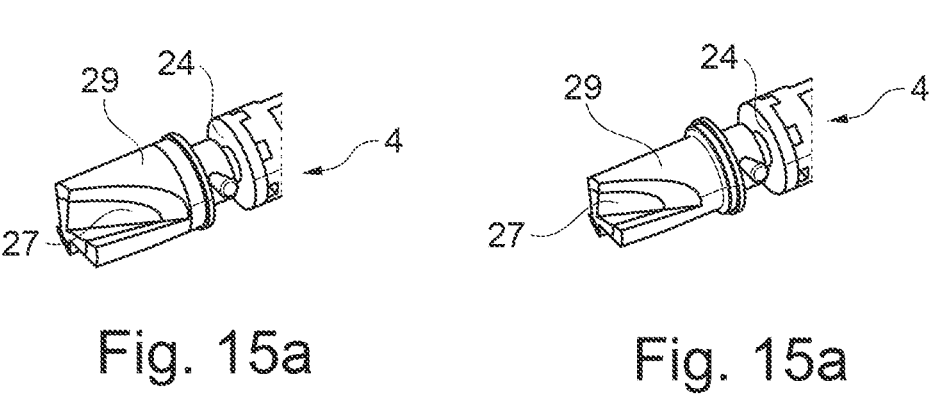
Figure 15C:
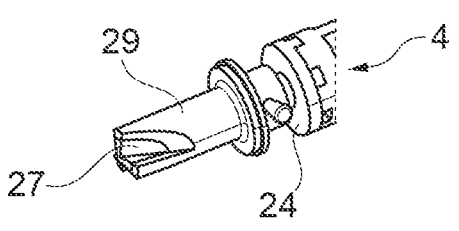
Figures 16A, 16B, 16C:
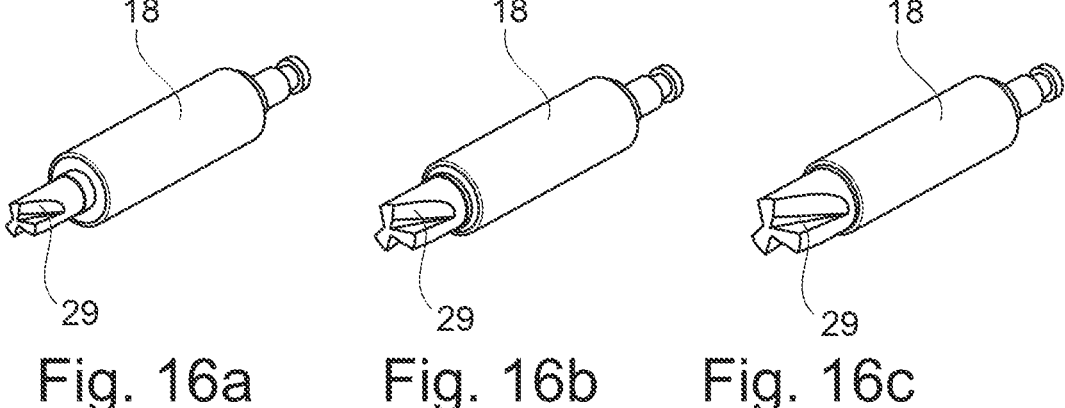

FIGS. 14 to 16 show the structure of the cutting portion 4 in accordance with a further aspect of the invention. As described above, the cutting portion 4 comprises a basic portion 24 which is connected to the first engagement portion 27 via the first interface 26 and to the second engagement portion 29 via the second interface 28. Preferably, the basic portion 24, the first engagement portion 27, and the second engagement portion 29 are designed as metal components. The basic portion 24 serves as a power transmission single part and is of equal design for cutting portions 4 of different size. Via the first interface 26 it is possible to screw first engagement portions 27, i.e. internal cutters, of different size onto the thread. Via the second interface 28 it is possible to push up second engagement portions 29, i.e., external cutters, of different size (cf. FIGS. 15*a* to 15*c*). The outer diameter of the flange 31 of the second engagement portion 29 is of equal design for differently large second engagement portions 29. Thus, it is possible to use the same sleeve portion 18 for cutting portions 4 of different size (cf. FIGS. 16*a* to 16*c*).

Figures 17, 18:
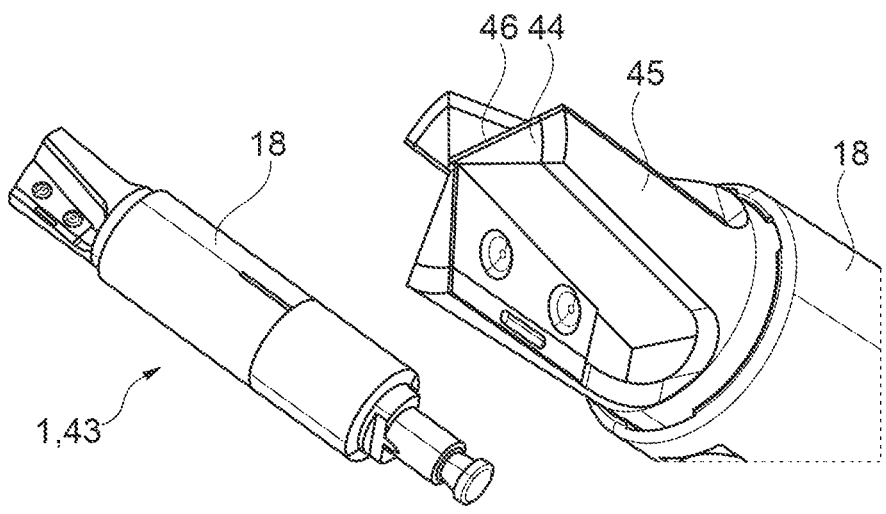
FIGS. 17 and 18 are perspective illustrations of the tool in a further embodiment.

FIGS. 17 and 18 show a further embodiment in accordance with a further aspect of the invention. The tool 1 is, apart from its blades, completely designed as a plastic component tool 43. The first engagement portion 27 is designed as a plastic component 44, like a plastic dome. The second engagement portion 29 is designed as a plastic component 49, like a plastic dome. An insert component 46 of metal is connected to the first engagement portion 27 and/or the second engagement portion 29 by thermal punching.

The invention claimed is:

1. A medical tool which is in the form of a rotatably drivable tool, the medical tool comprising:
   a drive portion configured to be connected to a medical device for interlockingly transmitting torque;
   a sleeve, the sleeve having an activating portion;
   a cutting portion configured to be coupled to the drive portion so as to transmit torque;
   wherein the cutting portion is displaceable relative to the drive portion between a first axial position, in which the cutting portion and the drive portion are rotationally-coupled and the cutting portion and the sleeve are rotationally-decoupled, and a second axial position, in which the cutting portion and the drive portion are rotationally-decoupled and the cutting portion and the sleeve are rotationally-decoupled, and
   an electronic assembly comprising a first switch that is configured to be activated mechanically by rotation of the activating portion, such that the electronic assembly is configured to acquire a number of revolutions of the cutting portion in the second axial position.

2. The medical tool according to claim 1, wherein the drive portion comprises a radial outer circumference and a push button radially outwardly projecting from the radial outer circumference, the push button forming the first switch, and wherein the sleeve comprises a radial inner circumference and a pin radially inwardly projecting from the radial inner circumference, the pin forming the activating portion.

3. The medical tool according to claim 2, wherein the drive portion comprises a radial circumferential groove, wherein the pin of the sleeve engages with the radial circumferential groove for axial locking engagement of the drive portion and the sleeve.

4. The medical tool according to claim 3, wherein the push button of the drive portion is positioned in the radial circumferential groove of the drive portion.

5. The medical tool according to claim 1, wherein the drive portion comprises a drive portion follower and the cutting portion comprises a cutting portion follower, the drive portion follower and the cutting portion engaging in the first axial position, wherein the sleeve radially encloses the drive portion follower and the cutting portion.

6. The medical tool according to claim 1, wherein the electronic assembly comprises a second switch, the second switch being mechanically activated by an axial displacement of the cutting portion from the first axial position to the second axial position such that a decoupling of the cutting portion from the drive portion is acquired.

7. The medical tool according to claim 6, wherein the electronic assembly is configured to acquire a number of decouplings of the cutting portion from the drive portion.

8. The medical tool according to claim 1, wherein the electronic assembly is arranged in a stationary component of the medical tool.

9. The medical tool according to claim 1, wherein the sleeve is made from plastic.

* * * * *